United States Patent [19]
Acevedo et al.

[11] Patent Number: 6,156,514
[45] Date of Patent: Dec. 5, 2000

[54] METHODS FOR MAKING RECOMBINANT CELLS

[75] Inventors: Jorge L. Acevedo; Peter R. Rhode, both of Miami, Fla.

[73] Assignee: Sunol Molecular Corporation, Miramar, Fla.

[21] Appl. No.: 09/204,979

[22] Filed: Dec. 3, 1998

[51] Int. Cl.$^7$ ..................................................... C12Q 1/68
[52] U.S. Cl. ............................... 435/6; 435/440; 435/325
[58] Field of Search ................................. 435/6, 440, 325

[56] References Cited

U.S. PATENT DOCUMENTS

| | | | |
|---|---|---|---|
| 4,766,067 | 8/1988 | Biswas | 435/69.1 |
| 4,956,288 | 9/1990 | Barsoum | 435/440 |
| 5,238,820 | 8/1993 | Kaufman | 435/69.1 |
| 5,420,019 | 5/1995 | Theofan et al. | 435/69.1 |
| 5,585,237 | 12/1996 | Oppermann et al. | 435/6 |
| 5,631,158 | 5/1997 | Dorai et al. | 435/440 |
| 5,639,275 | 6/1997 | Baetge et al. | 604/891.1 |
| 5,686,263 | 11/1997 | Wurm | 435/69.1 |
| 5,733,761 | 3/1998 | Treco et al. | 435/440 |
| 5,741,682 | 4/1998 | Lo et al. | 435/440 |
| 5,776,746 | 7/1998 | Denney, Jr. | 435/440 |

FOREIGN PATENT DOCUMENTS

89/10959  11/1989  WIPO .

OTHER PUBLICATIONS

Mitchell Roff, "Homologous Recombination In CHO Cells", *Biopharm.* (1988), V. 11, No. 7: pp. 34–35.

Florian M. Wurm, et al. "Gene Transfer and Amplification In CHO Cells", *Annals New York Academy Of Sciences*, pp. 70–78.

Martin Montoya–Zavala, et al. "Increased TPA Expression In C127 Cells Have Been Sequentially Tranfected With Two Different BPV Based Expression Vectors", *J. Cell Biochem.* Suppl. #13 Part C (1989), p. 210.

J. Barsoum, "Introduction Of Stable High–Copy–Number DNA Into Chinese Hamster Ovary Cells By Electroporation", *DNA And Cell Biol.*, vol. 9, No. 4, 1990, Mary Ann Liebert, Inc., Publishers, pp. 293–300.

*Primary Examiner*—James Ketter
*Attorney, Agent, or Firm*—Robert L. Buchanan; Peter F. Corless; Dike, Bronstein, Roberts & Cushman, LLP

[57] ABSTRACT

Disclosed are methods for producing recombinant cells and especially recombinant mammalian cell lines with enhanced expression of an amino acid sequence. Also disclosed are recombinant mammalian cell lines producing high levels of the amino acid sequence. The methods and recombinant cell lines of the invention have a number of useful applications including use in the efficient and large-scale production of recombinant proteins and polypeptides.

34 Claims, 4 Drawing Sheets

METHODS FOR MAKING RECOMBINANT CELLS

FIELD OF THE INVENTION

The present invention generally relates to methods for making recombinant cells expressing at least one amino acid sequence. The invention has a variety of useful applications including use in the production of recombinant mammalian cells that are stable and express high levels of a desired protein.

BACKGROUND OF THE INVENTION

There have been numerous attempts to produce high levels of a desired amino acid sequence by introducing a foreign (heterologous) nucleic acid into host cells and then expressing that nucleic acid inside the cells. Eukaryotic cells and especially mammalian cells have been employed with mixed results. For example, despite much effort toward improving methods of making recombinant mammalian cells that produce high levels of the amino acid sequence, most of the cells do not express the nucleic acid at sufficient levels. Thus, there is a need in the field to have methods for generating recombinant mammalian cells that express the introduced nucleic acid at high levels.

In general, two methods have been used to increase expression of heterologous nucleic acid in mammalian cells. One approach has been to enhance nucleic acid copy number by cell selection techniques such as drug resistance amplification. Another approach has been to increase expression of the nucleic acid inside the cells, e.g., by recombinantly adding one or more a beneficial control elements to that nucleic acid. See generally Kaufman, R. J. and P. A. Sharp (1982) *J Mol. Biol.* 159: 601; Sambrook et al. *Molecular Cloning* (2d ed. 1989) and Ausubel et al. *Current Protocols in Molecular Biology*, (19890 John Wiley & Sons, New York.

In particular, drug resistance amplification has been reported to involve cell transformation with two genes, one of which encodes an amino acid sequence of interest, such as a heterologous protein, and the other which encodes a selectable gene marker such as dihydrofolate reductase (DHFR). In instances in which The gene marker is DHFR, transformed cells are cultured in the presence of the selecting drug methotrexate (MXT). The normally cytotoxic effects of MTX are substantially eliminated by expression of the DHFR. Transformed cells survive because they have increased (amplified) DHFR copy number to a sufficiently high level. Nucleic acid sequence encoding the desired amino acid sequence is also amplified, thereby boosting expression of that sequence. See e.g., Kaufman, R. J. and P. A. Sharp, supra.

However, drug resistance amplification and related techniques have recognized drawbacks. For example, generation of most recombinant mammalian cell lines using the technique is time-consuming and may require several months to perform. Additionally, there has been recognition that when the heterologous nucleic acid is amplified, standard nucleic acid sequencing methods can be negatively impacted. Further, it is can be quite difficult to maintain sufficient nucleic acid copy number without imposing severe and sometimes long-term selection pressure. A cell selection strategy calling for extended selection pressure can be expensive and may present regulatory issues such as when a heterologous protein is being produced for pharmaceutical use.

In addition, drug resistance amplification may not be able to enhance expression of specific heterologous nucleic acids to levels sufficient for applications such as commercial or research use.

Further problems with drug resistance amplification include genetic instability of cloned cell lines. These problems are highly significant. For example, the method often produces recombinant cells that evolve from unstable gene amplification events, e.g., formation of double minute chromosomes. These cells can lose desired characteristics when the selecting drug is removed. See Kaufman, R. J. et al. (1985) *Mol. Cell. Biol.* 5: 1750 and references cited therein.

Additionally, optimal practice of most drug resistance amplification techniques has required use of highly specialized cells, vectors and/or cell growth conditions. For example, most of the methods employ host cells that have been genetically manipulated in specific ways. Such mutant cells may not be suited for some applications. As an illustration of the difficulties, drug resistance amplification involving DHFR and MTX will not work optimally in cells carrying a normal DHFR gene. Disabling that normal gene can be a lengthy and laborious process. See e.g., Wigler e. al. (1980) *PNAS* (USA) 3567; and Urlaub and Chasin, (1980) *PNAS* (USA) 77:4216.

More particular drawbacks of DHFR/MTX amplification methods relating to use of specific vectors and growth conditions have been disclosed. See e.g., Kaufman and Sharp, supra; Schimke, R. *Cell* (1984) 37:705. See also U.S. Pat. Nos. 5,686,263; 4,956,288 and 5,585,237 and references cited therein.

It would be useful to have methods for making recombinant cells that are flexible and can be used to produce recombinant cell lines that are genetically stable. It would be particularly desirable to have methods for producing recombinant mammalian cell lines that significantly reduce or avoid use of highly specialized cells, vectors and/or growth conditions. It would be further desirable to have recombinant mammalian cell lines made by those methods that produce high levels of an amino acid sequence of interest such as a heterologous protein.

SUMMARY OF THE INVENTION

The present invention relates to methods for producing, recombinant cells and particularly to methods for producing recombinant cell lines that are genetically stable and express high levels of at least one amino acid sequence. In one aspect, the invention provides methods for producing recombinant cell lines that express high levels of a heterologous protein. The methods generally involve introducing into host cells at least one vector encoding the amino acid sequence and subjecting the cells to conditions conducive to isolating recombinant cell lines that produce high levels of that sequence. Preferred methods produce high levels of the amino acid sequence while significantly reducing use of highly specialized host cells, vectors and/or growth conditions. Additionally provided are recombinant mammalian cell lines produced by the methods of this invention.

The present invention more particularly relates to methods for generating recombinant mammalian cell lines that are genetically stable and express high levels of at least one amino acid sequence of interest. In one embodiment, expression of the amino acid sequence is substantially enhanced by introducing into host cells a first vector encoding the sequence. The first vector includes at least one selectable sequence, typically a first selectable sequence, operably linked to a segment encoding the amino acid sequence. Additionally, the first vector may encode more than copy of the amino acid sequence if desired. The first vector can be introduced into the host cells once (singly) or more than once (multiply) as needed. The host cells are then cultured under conditions conducive to expressing the amino acid sequence followed by isolation of recombinant cell lines (first high expressing cells) expressing the sequence at a first high expression level.

The method further includes introducing, preferably into the first high expressing cells, a second vector encoding the amino acid sequence. The second vector may be the same or different from the first vector and it may encode more than one copy of the amino acid sequence if needed. The second vector is introduced into the first high expressing cells once (singly) or more than once (multiply) as needed. Recombinant cells comprising the second vector are then cultured under conditions conducive to expressing the amino acid sequence. Cells expressing the amino acid sequence at a second high expression level (second high expressing cells) are subsequently isolated.

As discussed, there has been recognition that cell lines made by prior cell selection schemes and especially drug resistance amplification techniques have suffered from drawbacks. Specific drawbacks include genetic instability and the need to use highly specialized cells, vectors and/or growth conditions. The present methods significantly avoid these drawbacks by providing genetically stable cell lines that produce high levels of the amino acid sequence. Further, the present methods are generally more flexible than the prior schemes and are compatible with a wide spectrum of vectors. Nearly any transfectable cell can be used with the present methods including most primary, secondary or cultured mammalian cells. Suitably, the present methods provide for growth of a specific transfectable mammalian cell under a variety of selective or non-selective growth conditions as needed.

More particular flexibility is provided by providing for either direct or indirect selection of recombinant cell lines expressing high levels of the amino acid sequence. For example, in one embodiment of the present methods, recombinant mammalian cell lines are selected indirectly by selection of at least one vector-encoded cell surface marker. Selection of that cell surface marker in accord with the invention facilitates efficient isolation of cell lines that express the amino acid sequence at high levels. As discussed, resulting cell lines are genetically stable and can be produced while minimizing or eliminating use of highly specialized cells, vectors, and/or growth conditions.

In a particular embodiment of the method, the second high expression level is substantially higher than the first high expression level by at least from about 2 to 10 fold higher or more. Methods for determining levels of amino acid sequences such as proteins are known in the field and include certain techniques such as antibody reactivity.

In a more particular embodiment, the method further includes introducing into the second high expressing cells, a third vector encoding the amino acid sequence and subjecting the cells to conditions conducive to expressing the amino acid sequence at a third expression level higher than the second expression level. Cells expressing the amino acid sequence at the third expression level are then isolated to produce the cell line (third high expressing cells). The third vector preferably encodes at least one amino acid sequence of interest and it can be the same or different from the first or second vector (or both vectors). The third vector can be introduced into the second high expressing cells once (singly) or more than once (multiply) as needed. The third high expressing cells will typically exhibit increased expression of the amino acid sequence when compared to the first or second high expressing cells.

In another particular embodiment, the method further includes introducing into the third high expressing cells at least one vector encoding the amino acid sequence, preferably one of such vectors, and subjecting the cells to conditions conducive to expressing the amino acid sequence at a level higher than the third expression level. The method further includes repeating the introduction and subjecting steps at least once, preferably from between about 2 to 10 times or more, to isolate a cell line expressing the amino acid sequence at a higher level than the third high expressing cells. Choice of how many times the steps are repeated will be guided by several parameters but particularly by the level of expression required.

In another embodiment, the step of culturing the host cells under conditions conducive to selecting the first vector further includes growing the host cells in selective media. Preferably, that selective media includes at least one drug and usually one drug selective for the first selectable sequence. It will be appreciated that vectors disclosed herein that include a selectable nucleic acid sequence, e.g., the first and fourth vectors, usually encode an amino acid sequence that is selectable. Illustrative drugs for selecting the vectors are described in the discussion and examples that follow.

It will often be preferred that the second or third vector (or both of the vectors) be co-introduced into cells with at least one other vector (sometimes referred to herein as "fourth" or "fifth" vector), which vector encodes at least one selectable sequence and particularly a selectable cell surface marker such as a cell surface protein. It has been surprisingly found that by co-introducing the vector encoding the selectable cell surface marker, it is possible to facilitate production of highly useful recombinant mammalian cell lines expressing high levels of the desired amino acid sequence. For example, it has been found that by co-introducing that vector in accord with the invention, it is possible to generate cell lines while reducing or totally eliminating the need to use highly specialized cells, vectors and/or growth conditions. Additionally, production of genetically stable recombinant cells is favored by practice of the methods.

In another embodiment of the method, the step of introducing the second vector into the first high expressing cells further comprises introducing the fourth vector into the cells. As discussed, the fourth vector encodes at least one selectable sequence (referred to herein as the "second" selectable sequence) preferably a selectable cell surface marker. The fourth vector may be the same as another vector of the method although in most cases the fourth vector will be different from any one or all of these vectors. In another embodiment, the fourth vector comprises a second selectable sequence operably linked to a segment encoding the amino acid sequence of interest. In a more specific embodiment, the method further includes growing the cells in selective media including at least one drug selective for the second selectable sequence.

In embodiments in which the fourth vector encodes the cell surface marker, the method preferably further includes isolating the cells expressing that selectable cell surface marker by at least one of chromatography, cell panning, flow cytometry, antibody binding, immunoprecipitation, or antibody binding. Usually one of these techniques will be employed to isolate the cells expressing the cell surface marker. By conducting the isolation, cell lines expressing high levels of the amino acid sequence encoded by the vectors is obtained.

In another embodiment of the method, the step of introducing the third vector into the second high expressing cells further includes introducing into the cells a fifth vector. In a particular embodiment, the fifth vector encodes at least one selectable sequence (referred to herein as the "third" selectable sequence). The fifth vector may be the same or different from any of the vectors disclosed herein. In a more particular embodiment, the fifth vector includes a third selectable sequence which if desired can be operably linked to a segment encoding the amino acid sequence. The cells are then subjected to conditions conducive to expressing the amino acid sequence at a third expression level higher than the second expression level. Preferably, the method further comprises growing the cells in selective media that includes at least one drug and preferably one drug selective for the third selectable sequence.

An additionally preferred fifth vector further includes a sequence encoding a selectable cell surface marker which can be the same or different from the cell surface marker encoded by the fourth vector. If desired, the selectable cell surface marker can be operably linked to a segment encoding the amino acid sequence. The method preferably further includes the step of isolating the cells expressing the selectable cell surface marker encoded by the fifth vector and using at least one of chromatography, cell panning, flow cytometry, antibody binding, immunoprecipitation, or antibody binding to isolate cells expressing the cell surface marker expressed by the fourth or fifth vector (or both vectors) as needed. By performing the isolation, recombinant cell lines expressing high levels of the amino acid sequence encoded by the vectors is obtained.

More particular second high expressing cells in accord with the invention generally express at least about 2 fold more of the amino acid sequence than the first high expressing cells as determined by standard protein quantitation techniques such as quantitative gel electrophoresis, chromatography and immunological techniques such as Western immunoblot, ELISA and antibody reactivity. More particular second high expressing cells express from between about 3 to about 40 fold of the amino acid sequence when compared to the first high expressing cells as determined by antibody reactivity.

Third high expressing cells of particular interest generally express at least about 2 fold more of the amino acid sequence than the second high expressing cells as determined by the standard protein sequence quantitation techniques. More particular third high expressing cells express from between about 3 to about 40 fold of the amino acid sequence when compared to the second high expressing cells as determined by antibody reactivity.

In a more specific embodiment of the methods, each of the first, second or third vectors independently encodes a first drug resistance gene (sometimes referred to herein as a gene marker), a selectable cell surface marker and a second drug resistance gene, respectively. In this embodiment, each of the vectors is operably linked to a segment encoding the amino acid sequence of interest. Additionally, the fourth and fifth vectors can each independently encode a third drug resistance gene and another cell surface marker, respectively. The first, second and third drug resistance genes can be the same or different as needed. Illustrative drug resistance genes and selectable cell surface markers are described in more detail below.

As an illustration of the invention, a suitable mammalian an host cell is first selected that does not require highly specialized vectors or growth conditions to optimally express a heterologous protein. Preferred mammalian host cells do not express the heterologous protein at detectable levels. However in some instances, suitable mammalian host cells may already express the protein as a homologous protein, e.g., at background (ie. basal) levels. In this instance, the invention can be used to boost expression of the homologous protein to levels higher than the basal levels. Alternatively, the present methods can be used to boost cell expression of a desired heterologous protein or polypeptide sequence. More specific mammalian host cells are provided below.

Following introduction of the first vector into the mammalian host cells, the first high expressing cells are isolated in growth media that is generally selective for the first vector. Second high expressing cells are produced by introducing the second vector encoding the amino acid sequence into the first high expressing cells. In one embodiment, the first and second vectors encode one copy of a heterologous protein and are substantially the same. Introduction of the second vector is accompanied by introduction of another ("fourth") vector encoding the selectable cell surface marker. Isolation of the second high expressing cells is performed under conditions conducive to selecting that cell surface marker and may optionally include growth in selective media if desired. In this embodiment, selection of the cell surface marker also selects for high co-expression of the desired amino acid sequence encoded by the first and second vectors. Use of highly specialized host cells, vectors and growth media to select the cells is significantly reduced in this example.

The present invention can be used to make a wide spectrum of recombinant cells and particularly mammalian cell lines that express high levels of at least one desired amino acid sequence of interest or a portion of that amino acid sequence such as a functional protein fragment. For example, methods of the invention can be used to express amino acid sequences of immunological interest such as an immunoglobin chain (heavy or light) or functional fragments thereof. More specific amino acid sequences of interest are discussed below.

The present invention provides significant advantages when contrasted with prior cell selection techniques and especially conventional drug resistance amplification methods. For example, as discussed, practice of most drug resistance amplification methods generally requires use highly specialized cell lines, vectors and growth conditions. In most instances, the cells have been genetically manipulated to block resistance to a drug and may not always exhibit good growth characteristics. Further, such cells can be difficult to make and/or maintain and may be particularly unsuitable for many specific cell selection strategies. The present invention addresses these shortcomings by providing methods for generating recombinant cell lines that reduce or eliminate use of these highly specialized cell lines.

Further, the present methods maximize the genetic stability of resulting recombinant cell lines by introducing heterologous nucleic acid into the host cell genome. Formation of highly unstable chromosome formations is reduced and often totally avoided.

Additional advantages are provided by this invention. For example, the present methods are substantially more flexible than prior methods for generating recombinant mammalian cells and can be used with a variety of mammalian expression vectors. In contrast, most prior cell selection techniques such as drug resistance amplification are tailored for use with highly specialized vectors. As an illustration of the problem, there has been acknowledgement that vectors for many drug resistance amplification techniques have become too large and difficult to manipulate. Also many optimal vectors for use with prior cell selection schemes are proprietary and may not always be available when needed. The present invention solves this problem, e.g., by providing compatibility with a wide variety of mammalian expression vectors.

As discussed, at least one of the vectors described herein may encode a portion of the amino acid sequence of interest. As an illustration, for a specific full-length heterologous protein, the first vector can encode a first portion of that protein and at least one of the second, third, fourth and fifth vectors can encode other portions of that protein the same or different. In this example, the totality of the protein sequence encoded by the vectors will be substantially equivalent to the full-length protein. In another example, the first vector (or any other of the vectors) may encode the full-length and at least one other of the vectors, e.g., the second, third or fourth vector may encode a specific portion of the protein. The remaining vectors can be used, e.g., to introduce additional portions of the protein sequence or even the full-length protein sequence if desired.

The ability of the present methods to introduce portions of an amino acid sequence of interest provides advantages. For example, the methods can be used to provide highly controlled amplification of one or several portions of the amino acid sequence. That is, specific portions of the amino acid sequence including the entire sequence can be amplified in specific cells (e.g., first or second high expressing cells) prior to or concurrent with amplification of another sequence. The invention therefore provides for sequential and coordinate expression of one or even several amino acid sequences of interest.

As a more specific illustration, the first vector can encode a first subunit of a multi-subunit protein (homologous or heterologous) and the second vector can encode a second subunit of that same protein. In this example, first vector encoding the first subunit can be introduced into the host cells and the first high expressing cells selected. The second vector encoding the second subunit can be introduced into the first high expressing cells and the second high expressing cells selected that express both the first and second subunits. If, for example, the multi-subunit protein is a dimer, that protein can be specifically formed in the first high expressing cells under conditions of enhanced expression of the first and second subunits. Thus, the present invention is especially useful for analyzing assembly and stability of multi-subunit proteins under conditions of sequential and highly controlled subunit expression.

Particularly contemplated is sequential and highly controlled assembly of proteins of immunological interest such as immunoglobins and particularly immunoglobin heavy and light chains.

More generally, the present invention facilitates implementation of strategies for assembling the multi-subunit proteins by providing substantial flexibility and control over the amplification process. For example, the methods can be used to enhance production of the subunits, e.g., at predetermined high expression levels inside cells. In contrast, most prior techniques and particularly drug resistance amplification techniques are substantially less flexible and do not provide control over the subunit assembly.

In another aspect, the present invention provides cell lines and particularly recombinant mammalian cell lines that are produced by the methods disclosed herein. Such cell lines are genetically stable and are specifically selected to express the amino acid sequence or portion thereof at high levels.

The methods of this invention specifically provide for selection of recombinant mammalian cell lines that express at least heterologous protein at high levels.

Particular methods of this invention provide additional advantages. For example, practice of methods to generate recombinant mammalian cell lines (sometimes called "high producing cell lines" or related term) can be achieved in significantly less time than other cell selection methods including most prior drug amplification methods. In addition, the methods produce high producing cell lines by using fewer cell passages than most prior methods, thereby reducing labor and media costs.

DETAILED DESCRIPTION OF THE INVENTION

As summarized above, the present invention provides methods for making a wide spectrum of cells and particularly recombinant cell lines. Particularly provided are methods for making recombinant mammalian cell lines that are genetically stable and produce high levels of a heterologous or homologous protein of interest. As discussed, the invention is flexible and can be used to make highly useful cell lines that produce high levels of the protein while significantly avoiding use of highly specialized cells, vectors and/or growth conditions. Additionally provided are recombinant mammalian cell lines that produce high levels of the protein.

In general, optimal practice of the present invention is achieved by use of recognized manipulations. For example, techniques for isolating DNA, making and selecting vectors for expressing the DNA, purifying and analyzing nucleic acids, specific methods for making recombinant vector DNA, cleaving DNA with restriction enzymes, ligating DNA, introducing DNA including vector DNA into host cells by stable or transient means, culturing the host cells in selective or non-selective media, exemplary host cells methods for selecting and maintaining cells stably or transiently expressing the DNA, are generally known in the field. See generally Sambrook et al., supra; and Ausubel et al., supra.

The present invention provides, in one aspect, novel methods for generating recombinant mammalian cell lines. A recombinant mammalian cell line will sometimes be referred to herein as a "high producing" cell line or related term. The phrase "high level", "high producing" or the like, when used to reference the amount of an amino acid sequence produced by the cell line, means that at least about 2 fold and preferably from between about 3 to about 40 fold or higher (some heterologous sequences are not present in the parental cell line) more of the amino acid sequence is produced by the cell line compared to a parental cell or parental cell line.

Methods for determining the amount of a particular amino acid sequence produced by a recombinant cell line described herein are known in the field and include chromatographic methods such as protein gel electrophoresis and immunological techniques such as Western blotting and ELISA. More particular gel electrophoretic methods include those in which a protein or peptide sequence is detected and quantitated using Coumassie blue or silver staining. A preferred protein quantitation method is antibody reactivity.

By the term "antibody reactivity" is meant specific binding between a designated antibody and the amino acid sequence produced by the cell or cell line. The term is further meant to reference formation of a specific binding pair between the amino acid sequence (ie. an epitope thereon) and the antibody but which does not significantly bind to other molecules as determined, e.g., by Western blotting, ELISA, RIA, gel mobility shift assay, enzyme immunoassay, competitive assays, saturation assays or other suitable amino acid sequence binding assays known in the field. See generally, Harlow and Lane in *Antibodies: A Laboratory Manual*, CSH Publications, New York (1988), for disclosure relating to these and other suitable assays.

By the term "parental" as it is used to reference a host cell or cell line is meant an ancestor of that cell or cell line used to make a subsequent cell line. Illustrative parental cells are suitable host cells used to make the first high expressing cells. The first high expressing cells are in turn an example of a parental cell line used to make the second high expressing cells. It will be understood that a cell line is a clonal population of cells derived form a single ancestor cell unless otherwise stated. Methods for making cell lines are generally known in the field and include well-known serial dilution techniques. See e.g., Ausubel et al., supra.

In accord with one aspect of the invention, mammalian host cells providing enhanced expression of a specific amino acid sequence such as a heterologous protein are obtained by introducing into the cells a first vector that includes at least one selectable sequence and preferably one selectable sequence (first selectable sequence) operably linked to the segment encoding the protein. Following culturing and isolation of cells expressing the protein at the first high expression level (first high expressing cells), a second vector encoding the protein is introduced into the first high expressing cells. It is generally preferred that the introduction of the second vector be accompanied by introduction of another vector (ie. fourth vector) which encodes at least one and preferably one selectable cell surface marker. However, in other embodiments, the second vector encodes both the protein and at least one cell surface marker, preferably one of such markers. The cells are subjected to conditions conducive to expressing the amino acid sequence at a second expression level that is higher than the first expression level. Preferred conditions select for at least one of the cell surface markers and do not use highly specialized cells, vectors and growth conditions. A cell line expressing the protein at the second expression level is then isolated to produce the second high expressing cells.

By the term "isolated" as it refers to specific cells or cell lines disclosed herein means cells that have been purified to at least about 80 to 95% (w/w) homogeneity. Purified cells of higher purity, e.g., at least about 98% to 99% homogeneity (w/w) are more preferred for most applications. Once purified, the cells can be used for subsequent manipulations such as cell transfections or establishment of cell lines using recognized serial dilution techniques.

As discussed, the first and/or second vectors can be introduced into respective cells once (singly) or more than once (multiply), preferably from between about 2 to about 20 times and more preferably from between about 2 to 5 times, as needed. Choice of whether to introduce the first and/or second vector into respective cells once or more than once will be guided by several parameters such as the level of enhanced expression desired and the particular amino acid sequence of interest.

In a more particular embodiment, the conditions used to select the second high expressing cells include selection of at least one cell surface marker and preferably one cell surface marker, which marker is encoded by one of the vectors co-introduced into the first high expressing cells. As discussed, those vectors can be the fourth or fifth vector. It is emphasized that this embodiment of the present methods is a substantial improvement over prior expression systems such as drug resistance amplification techniques. For example, by co-introducing the vectors into the cells, selection of the second high expressing cells can be conducted by selection of the cell surface marker, thereby many of the problems already discussed. Also significantly, sequential introduction of the first and second vector in accord with this invention can enhance levels of expression of the amino acid sequence above the sum of the levels of the amino acid sequence.

An "amino acid sequence" generally refers to any polymer consisting essentially of any of the 20 amino acids regardless of its size. Although the term is used herein to reference proteins, the term will be understood to encompass polypeptides and peptides unless specifically stated otherwise. The amino acid sequence may encode a full-length protein (heterologous or homologous with respect to the expressing cell) or a portion thereof such as a functional fragment. More specific amino acid sequences are described below. A specifically preferred amino acid sequence is an immunoglobin heavy chain, light chain; or a functional fragment thereof.

By the term "functional fragment" as it is used with respect to an amino acid sequence is meant at least a segment of an amino acid sequence that has at least one of the activities of the full-length amino acid sequence. With respect to protein sequences, those activities include specific binding and enzymatic activity. Preferred functional fragments have at least about 70% and more preferably from between about 80% to 95% of the activity of the full-length protein as determined by a suitable assay.

By the term "operably linked" is meant linkage of polynucleotide elements in a functional relationship. A nucleic acid is "operably linked" in accord with this invention when it is placed into a functional relationship with another nucleic acid sequence. In particular, operably linked sequences may reside on the same vector or on different vectors within the same cell. For instance, a promoter or enhancer is operably linked to a specific coding sequence if it affects transcription of that coding sequence. That is, for this example, operably linked means that the DNA sequences being linked are contiguous and, where necessary to join two protein coding regions, contiguous and in reading frame. However, operably linked sequences may reside on different vectors in some instances. As an illustration, a vector sequence encoding one subunit of a multi-subunit protein would be operably linked to another vector sequence encoding another subunit (binding partner) of that protein.

Methods of the present invention are operable and highly useful with a wide spectrum of host cells, particularly those well adapted to tissue culture. Typically, the host cells are eukaryotic, preferably mammalian cells that exhibit good growth characteristics in standard media preparations. Substantially, nearly any non-microbial cell, whether or not previously transformed, and which can express a desired amino acid sequence at high levels can be used in accord with the invention. A variety of such cells are known in the art and include CHO, CV-1, HeLa and other cells. See generally Sambrook et al., supra and Ausubel et al., supra; and the American Tissue Type Culture Collection, 10801 University Boulevard, Manassas, Va.

As will become even more apparent from the discussion and examples which follow, a variety of vectors and especially mammalian expression vectors can be used with the present invention. Particular vectors will generally include suitable regulatory sequences for self-replication and preferably selection in a desired host cell or cell line.

The term "vector" is more particularly defined as any nucleic acid sequence of interest capable of being incorporated into a host cell and resulting in the expression of a nucleic acid sequence of interest. That nucleic acid sequence of interest will preferably encode all or a substantial part of the amino acid sequence described above. Suitable vectors can include but are not limited to linear nucleic acid sequences, plasmids, cosmids, phagemids, episomes and extrachromosomal DNA. Additionally included are viral DNA and viral RNA. Specifically, the vector can be a recombinant DNA. Also used herein, the term "expression" or "gene expression", is meant to refer to the production of the protein product of the nucleic acid sequence of interest, including transcription of the DNA and translation of the RNA transcript.

More particular vectors for use with the present invention include at least one selectable nucleic acid sequence, usually one of such a sequence. For purposes of illustration, selectable sequences are sometimes referred to as a selectable gene marker (or related term) when the sequence encodes an intracellular sequence; or cell surface marker (or related term) when the sequence encodes a cell surface protein.

It will be apparent that a wide variety of vector-encoded selectable sequences are compatible with the invention. Preferred vectors facilitate selection of host cells or cell lines that harbor the vector or other vectors co-introduced in the cell. That goal can be achieved by a variety of techniques including substantial survival of the cells following exposure to a cytotoxic drug. See generally, Southern, P.J. et al. (1982) *J. Mol Appl. Gen.* 1: 327; Sambrook et al. supra; and Ausubel et al. supra.

For example, illustrative selectable gene markers for use with this invention include DHFR, aminoglycoside antibiotic G418, hygromycin B (hmb), and neomycin phosphotransferase II gene (neo), puromycin and the adenosine deaminase gene for certain auxotrophic eukaryotic cells, e.g., Chinese hamster ovary (CHO) cells. It is contemplated that in some situations, the desired amino acid sequence encoded by the vector may itself be a sufficient selectable marker or may positively impact function of the selectable marker. In cases in which the amino acid sequence itself encodes the selectable marker, a separate selectable marker need not be included in the vector. See e.g., Southern, P.J. et al. (1981) *J. Mol. Biol.* 150:1; Sambrook et al., supra; and Ausubel et al. supra and references therein for additional disclosure relating to gene markers.

As discussed, the selectable nucleic acid sequence may encode a suitable cell surface marker and particularly a cell surface protein. Exemplary cell surface markers include a cell surface receptor, glycoprotein, carbohydrate, protein, lipoprotein, major histocompatibility complex (MHC/HLA), antibody, antigen or a functional fragment thereof. More particular cell surface markers include glycoproteins of immunological interest such as CD (cluster of differentiation) glycoproteins typically found on T-cell surfaces. Examples include CD2, CD3, CD4, CD8 and LFA-1. A more particular glycoprotein of interest is the CD4 molecule and especially a functional fragment of that molecule. See also the CaptureTec™ System provided by InVitrogen.

As discussed above in the examples that follow, cells that express a specific cell surface marker can be isolated by one or a combination of different strategies. For example, in one approach, the cells can be isolated by chromatography, cell panning, flow cytometry, antibody binding or immunoprecipitation. A preferred approach is chromatography involving magnetic selection as discussed below.

By the term "functional fragment" as the term is used to define a selectable cell surface marker is meant a portion of that marker, e.g., the CD4 glycoprotein, which is capable of specifically binding another immunological molecule such as an antibody like a monoclonal antibody. The term is also meant to include nucleic acid sequence encoding the functional fragment.

In general, once a suitable selectable sequence is chosen, it will be operably linked to one or more regulatory sequences so that the encoded amino acid sequence is positioned in the vector, e.g., adjacent to a promoter. In this way, expression of the desired amino acid sequence is facilitated. It is contemplated that some amino acid sequences such as a heterologous or homologous protein will have its own cell or tissue specific promoter. Further included regulatory sequences are suitable leader and polyadenylation sequences.

In more particular examples of the present invention, expression of the amino acid sequence is either as a mono- or di-cistron as needed. For example, expression is monocistronic when the promoter is operably linked to both the selectable nucleic acid sequence and the amino acid sequence of interest, e.g., promoter/encoded amino acid sequence/selectable nucleic acid sequence; promoter/selectable nucleic acid sequence/encoded amino acid sequence. Alternatively, dicistronic expression follows from expressing the amino acid sequence from separate promoters, e.g., promoter/encoded amino acid sequence or selectable nucleic acid sequence.

As discussed, the present methods are compatible with a wide variety of vectors. These vectors typically encode the amino acid sequence (or several of such sequences) for which enhanced expression is desired. A preferred vector format is sometimes referred to as expression cassette. In one embodiment, the expression cassette generally includes a promoter functional in the cell or cell line hosting the vector, an operator, a ribosomal initiation site, the amino acid sequence, and an sufficient 3' portion encoding polyadenylation signals to facilitate processing and, in some cases, secretion of the amino acid sequence from the cell. A preferred example of a terminator sequence is the polyadenylation sequence from SV40. If desired, the expression cassette or other appropriate portion of the vector may include a signal sequence near the 5' end of the amino acid sequence to facilitate post-translational processing of that sequence. At least one suitable gene marker or cell surface vector can be positioned in the vector if needed.

A more specific example of a suitable vector including the expression cassette is a DNA vector comprising (i) an origin of replication (Ori) functional in E. coli; (ii) a selectable gene marker (antibiotic resistance gene e.g., Amp, Tet, Neo or Kan resistance); (iii) a strong viral promoter such as the cytomeglovirus (CMV) promoter and optional CMV enhancer element, (iv) an (Ig-$C_L$) immunoglobin light chain constant region leader sequence, (v) the amino acid sequence of interest, (vi) a full-length Ig-$C_L$ intron linked to an Ig-$C_L$ exon, (vii) a growth hormone polyadenlyation sequence, e.g., bovine growth hormone (bgh) poly A sequence and (viii) DNA encoding a selectable eukaryotic marker such as a strong viral promoter (e.g., simian virus 40 (SV40) promoter, linked to the antibiotic resistance gene fused to a viral polyadenlyation sequence (e.g., the SV40 polyA sequence). Alternatively, the DNA vector can include all of (i)–(v), and (vii)–(viii), above, without the full-length Ig-$C_L$ intron linked to the Ig-$C_L$ exon of (vi). An exemplary Ig-$C_L$ leader sequence is the mouse kappa leader. An example of a full-length Ig-$C_L$ intron and exon is the full-length Cκ gene.

The amino acid sequence for which enhanced expression is desired can be nearly any protein or polypeptide sequence including heterologous proteins or homologous (endogenous) proteins naturally produced by the host cell. In most cases, the amino acid sequence will be a eukaryotic protein including, but not limited to, a subunit or functional fragment of a larger amino acid sequence such as a multi-subunit protein. More specific amino acid sequences include enzymes, immunoglobulins, peptide hormones, vaccines, receptors, including T-cell receptors, MHC/HLA molecules (class I and class II); or fragments thereof. Additionally specific proteins include growth factors, blood coagulation factors, cytokines, e.g., plasminogen activator, tissue factor (TF), insulin, mammalian growth hormone, erythropietin, IgE, urokinase, interleukins 1, 2, and 3; or fragments thereof. The invention is further compatible with other known, partially known, or unknown amino acid sequences including those encoding novel gene sequences.

A variety of such amino acid sequences can be found, e.g., in Genbank (National Library of Medicine, 38A, 8N05, Rockville Pike, Bethesda, Md. 20894). Genbank is also available on the internet at http://www.ncbi.nlm.nih.gov.

Molecular weights of specific vectors discussed herein can be determined by conventional techniques such as agarose gel electrophoresis sizing and will vary depending, e.g, on intended use. However, most suitable vectors and especially suitable DNA vector will have a molecular weight of at least about 5 kb and particularly from between about 5 kb to about 35 kb or higher. The molecular weight of particular amino acid sequences can be determined by standard protein sizing techniques such as polyacrylamide gel electrophoresis. Alternatively, or in addition, the molecular weight can be estimated by determining the molecular weight of the corresponding nucleic acid sequence followed by conceptual translation of that sequence. For most applications, the size of the nucleic acid encoding the amino acid sequence will be sufficient to encode a protein or polypeptide of from between about 500 to about 300,000 daltons with about 15 to about 200,000 daltons being generally preferred.

See the following examples for more specific vectors for use with this invention such as pJAIgG4Tf.A8, pDRHK, and pMACS. See also FIGS. 1A and 1B. In particular, the pDRHK vector has been deposited pursuant to the Budapest Treaty with the ATCC at the address disclosed above. The DNA vector was deposited with the ATCC on Sep. 17, 1997 and was assigned Accession No. 209274. The pDRHK vector is a mammalian expression vector which includes a CMV promoter, mouse IgC kappa leader peptide, cloning region, mouse kappa intron and human kappa constant domain exon sequence.

As discussed above, the present invention features a series of recombinant manipulations involving sequential and co-ordinate vector introduction to generate recombinant mammalian cell lines that express high levels of an amino acid sequence. Introduction of the vectors can be achieved by a variety of ways including retroviral transfer, viral infection, calcium-, liposome-, or polybrene- mediated transfection, biolistic transfer, or other such techniques known in the art. More preferred introduction methods include those adaptable for stable transfection of mammalian cells such as electroporation. However, for some applications it may be useful to employ at some transient introduction methods provided the resulting recombinant cell lines are genetically stable.

As a more specific illustration of the invention, a suitable mammalian host cell such as CHO is transfected once (singly) or at least twice (multiply) with suitable vectors each including at least one selectable marker and encoding at least one heterologous protein of interest. In a more specific embodiment, the host cells are transfected with one vector that includes a first selectable sequence (gene marker) operably linked to a segment operably linked to the encoded protein. A variety of transfection methods can be used to introduce the vector into the host cells such as standard calcium phosphate mediated transfection or lipofection techniques. Transfected host cells are then subjected to selective growth conditions so that first high expressing cells can be isolated. Methods for isolating transfected cells have been described in e.g., Sambrook et al., supra; Ausubel et al. supra; and in Wigler *PNAS* (USA) (1979) 76: 1376.

The first high expressing cells are isolated and can be characterized if desired by one or a combination of standard techniques. For example, in one approach, the CHO cells are transfected with a vector encoding a neomycin gene marker (providing G418 resistance) operably linked to a protein sequence such as an immunoglobin-encoding sequence and particularly a sequence encoding an antibody. Transfected host cells expressing the protein sequence are then cloned by standard techniques (e.g., limiting dilution and grow-up) performed in microtitre tissue culture plates. After incubating the cells for about a few days up to a few weeks or longer, single colonies will typically appear. Preferably only single colonies are used for additional manipulations. High producing clones are selected by any acceptable method such as standard immunological methods and particularly an ELISA assay. Preferred are ELISA assays optimized to detect and quantitate antibody production. Preferred high producing cells are those that produce substantially the highest amount of antibody in the ELISA assay. More preferred are first high producing cells producing from between about 0.5 to about 20 micrograms antibody per milliliters of media. Specifically preferred are first high producing cells producing from between about 1 to about 5 micrograms antibody per milliliters of media.

The first high producing cells are further manipulated particularly to increase cell copies of nucleic acid encoding the protein sequence. A specific goal in this example is to produce a genetically stable antibody producing cell line. In one embodiment, the first high producing cells are further transfected, e.g., by electroporation, with two different vectors: one encoding the protein sequence and the other vector encoding a suitable cell surface marker such as a glycoprotein and especially CD4 or a fragment thereof. See FIG. 1A. A preferred commercially available vector encoding the CD4 is pMACS (see below). In this example, transfectants are treated with a specific antibody or suitable antigen binding fragment thereof capable of specifically binding the cell surface protein.

By the term "genetically stable" as it is meant herein to refer to a cell means a cell that is substantially free of genomic rearrangements that include the heterologous nucleic acid. Particularly avoided rearrangements include double-minute chromosomes. The present methods preferably introduce the heterologous nucleic acids into the hosting cell genome to maximize genetic stability.

The specific binding between cells expressing the cell surface protein from one of the vectors and the protein sequence encoded by the other vector can be detected in a variety of ways including standard immunological techniques such as chromatography and especially column chromatography involving magnetic beads. In this approach, the antibody targeted against the cell surface protein is covalently attached to the magnetic beads, thereby allowing any cells expressing the cell surface protein to be isolated by applying a magnetic field to the cells and the magnetic beads. Bound cells are then removed from the column and grown in microtitre tissue culture plates. Optionally, the cells can be grown in selective media such as G418 supplemented media.

The second high producing cells can be isolated by several techniques. For example, in one particular approach, the cells are grown in the walls for a time sufficient to allow antibody production and secretion into the culture media. A suitable anti-diotypic antibody against an Fc portion is coated to the microtitre culture plate wells and the cell culture media is added thereto. The media including high levels of the antibody can be detected by standard techniques such as conventional sandwhich type assays using a suitable secondary antibody labeled with, e.g., horseradish peroxidase (HRP). Preferred second high producing cells are isolated by identifying high antibody production rates to cell number in the plate. Methods for performing this analysis are described in more detail below and specifically include an ELISA detection format. Preferred are second high producing cells producing from between about 0.1 to about 10 micrograms antibody or more per $10^6$ cells over about a 24 hour period. A more preferred range is between about 1 to about 5 micrograms antibody per $10^6$ cells over about a 24 hour period.

As discussed, additionally preferred are second high producing cells that produce from between about 3 to about 40 fold or more of the antibody when compared to the first high producing cells. Antibody reactivity is a preferred method of making this determination.

Second high expressing cells are further transfected to provide for isolation of cell lines that express more of the protein, e.g., the third high expressing cells. For example, to increase production of the antibody in the second high cells, the two vectors used to transfect the first high expressing cells are again used again to co-transfect the second high expressing cells. A preferred transfection method is electroporation although other transfection methods could be used if desired. High producing cells making increased levels of the antibody can be isolated as discussed above involving magnetic column chromatography of CD4 expressing cells followed by isolation of high producing cells. Optionally, the cells can be grown in non-selective or selective media such as G418 supplemented media. Preferred high producing cells produce maximal levels of antibody as determined by identifying high antibody production rates to cell number in the plate.

In this example, selected cell lines are preferably serially diluted and grown by conventional methods in microtitre tissue culture plates. After about a few days up to a few weeks or more, antibody production is tested by a suitable immunological technique such as ELISA. Clones with high antibody production levels are further amplified. Preferred are clones having from between about 1 to about 100 micrograms antibody or more per $10^6$ cells over a 24 hour period. A more preferred range is from between about 15 to about 50 micrograms antibody per $10^6$ cells over a 24 hour period. Additionally preferred are clones that exhibit at least about 2 fold up to about 10 fold more antibody production than the second high producing cells.

Selected clones satisfying the above criteria are preferably serially diluted according to standard methods. After a few days up to a few weeks or more, single colonies are tested for antibody production by a suitable immunological method such as ELISA. The highest producing clone (third high expressing cell) is selected for preparation of static cultures as described in detail below. Preferred third high expressing cells produce from about 20 to about 200 micrograms per milliliter of culture. More preferred third high expressing cells produce from about 50 to 150 micrograms per milliliter of culture with about 100 micrograms per milliliter of culture being generally preferred.

Additionally preferred are third high producing cells produce from between about 3 to about 40 fold or more of the antibody when compared to the second high producing cells as determined by antibody reactivity.

Additionally preferred are third high producing cells produce from between about 10 to about 200 fold or more of the antibody when compared to the first high producing cells as determined by antibody reactivity.

Figure 1A:
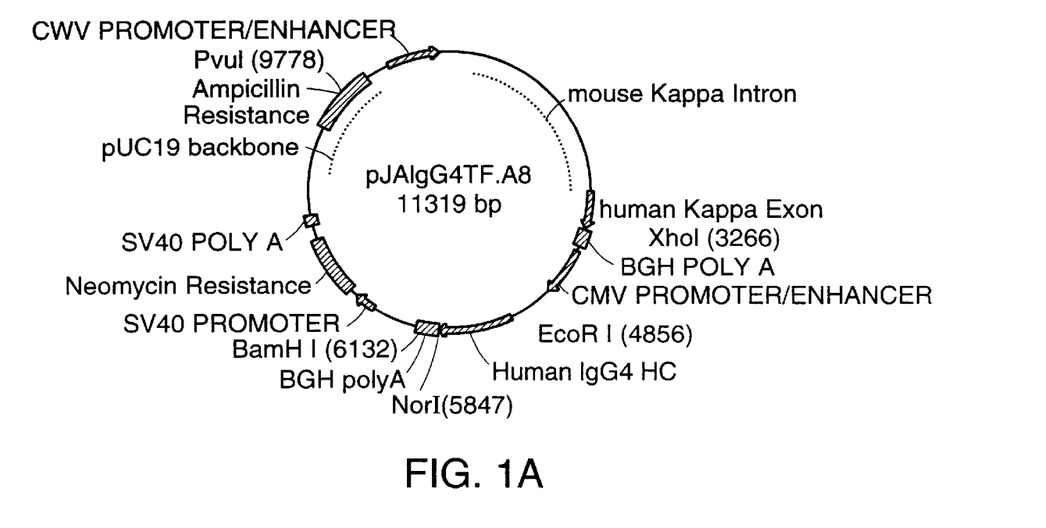
FIGS. 1A and 1B are drawings showing illustrative vectors for use with the invention. (1A) vector pJAIgG4TF encodes a chimeric anti-tissue factor (TF) heavy and light immunoglobin chains. (1B) vector pDRHK encodes a single-chain HLA-DR2/MBP molecule fused to a human immunoglobin kappa constant domain.

A specific example of a suitable antibody is the anti-TF antibody encoded by the pJAIgG4TF.A8 vector shown in FIG. 1A.

The high producing cell lines produced by the methods described herein have a number of highly useful applications including use in commercial, research and medical settings. For example, it has been found that the high producing cells generated by the method are especially amenable to commercial scale production of the protein sequence. As an illustration, the examples below describe use of a hollow fiber bioreactor to produce the protein sequence on a large-scale (ie. milligram amounts per ml).

In an specific example of the present invention, recombinant mammalian cell lines can be generated that produce high levels of MHC complexes and particularly recombinant MHC single-chain and heterodimeric complexes. These complexes have been disclosed, e.g., in co-pending U.S. application Ser. No. 08/382,454, filed on Feb. 1, 1995; Ser. No. 08/596,387, filed on Jan. 31, 1996; and PCT application WO 96/04314 published on Feb. 15, 1996; the disclosures of which are incorporated herein by reference. Particularly described in the pending U.S. application Ser. Nos. 08/382, 454 and 08/596,387 and published PCT application WO 96/04314 are a variety of single-chain MHC fusion complexes comprising a covalently linked presenting peptide.

For example, to generate recombinant mammalian cell lines expressing a desired single-chain MHC complex at high levels, a suitable mammalian host cell such as CHO is transfected once (singly) or at least twice (multiply) with suitable vectors. The vectors each include at least one selectable marker as defined above and at least one segment encoding the single-chain MHC complex. In preferred embodiments, the single-chain complex is class II although a class I single-chain complex may be preferred in some instances. The host cells are preferably transfected with one suitable vector encoding the single-chain complex operably linked to a selectable marker. A variety of transfection methods can be used such as standard calcium phosphate mediated transfection or lipofection techniques. Transfected host cells are then subjected to selective growth conditions so that first high expressing cells can be isolated. Methods for isolating transfected cells have been described in e.g., Sambrook et al., supra; Ausubel et al. supra; and in Wigler *PNAS* (USA) (1979) 76: 1376.

In a more specific method, the vector includes a selectable gene marker such as a neomycin gene operably linked to the single-chain MHC complex. Host cells are preferably transfected by electroporation and transfected host cells expressing the fusion protein sequence are cloned by limiting dilution methods performed in microtitre tissue culture plates. After incubating the cells for a day or so up to a few weeks or longer, transfected cells are harvested and diluted in non-selective or selective media such as G418 supplemented media. Supernatants are tested as described above and the examples which follow. High producing clones are selected and expanded. Selected clones are harvested and grown for several days up to a few weeks or more to isolate first high producing cells. Preferred are first high producing cells making from between about 1 to 100 nanograms of the fusion protein per ml of media. More preferred are first high producing cells producing from between about 10 to 50 nanograms per milliliter.

The first high producing cells making the single-chain MHC fusion protein are further manipulated as follows. The first high producing cells are further co-transfected, e.g., by electroporation, with two vectors: one that encodes that single-chain fusion protein and another vector that encodes a suitable cell surface protein such as a glycoprotein and especially CD4. A preferred vector encoding the CD4 is the commercially available pMACS vector (see below). Transfectants are subsequently treated with a specific antibody or suitable antigen binding fragment thereof capable of specifically binding the cell surface protein. The specific binding can be detected in a variety of ways, however, column chromatography involving magnetic beads is a preferred method. Bound cells are then removed from the column and grown in microtitre tissue culture plates. These second high producing cells can be grown in non-selective or selective media such as G418 supplemented media.

Static cultures of the second high producing cells can be made if desired. Preferred are second high producing cells that produce from between about 50 to 500 nanograms of the fusion protein per milliliter. More preferred ate high producing cells that produce from between about 100 to 200 nanograms of the fusion protein per milliliter.

To further increase production of the single-chain MHC complex, the second high producing cells can be additionally transfected. In one approach, the second high producing cells are co-transfected with a mixture of the vector encoding the single-chain MHC fusion protein and another vector carrying a selectable nucleic acid sequence that confers resistance to a drug such as puromycin or other suitable drug. The co-transfection can be performed by any suitable method including electroporation if desired. After incubation for a few days up to a few weeks or more, cells are harvested and resuspended in media supplemented with puromycin. After visualization of resistant colonies, culture media can be tested for production of the fusion protein, e.g, by ELISA. Static cultures can be made from clones producing high levels of the protein. Preferred third high producing cells produce from between about 500 to about 5000 nanograms per milliliter of the fusion protein. More preferred are third high producing cells that produce from between about 1000 to 2000 nanograms per milliliter of the protein.

If desired, suitable third high producing cells can be further subcloned to improve recombinant protein expression. A preferred method is limited dilution cloning. Additionally preferred are clones of the third high producing cells producing from between about 100 to about 1000 nanograms of the fusion protein per milliliter over 24 hours. Particularly preferred are the clones producing from between about 200 to 500 nanograms of the fusion protein per milliliter over 24 hours.

Figure 1B:
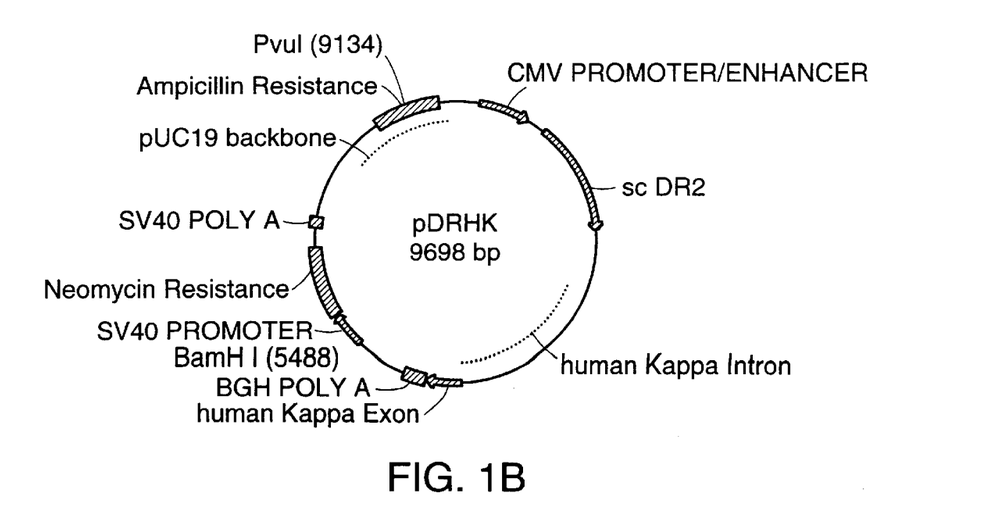

An example of a vector encoding a single-chain MHC complex is the pDRHK vector shown in FIG. 1B. That vector encodes a sc-DR2/MBP single-chain class II MHC complex.

The present methods can be varied to suit intended use. For example, the invention specifically encompasses the following embodiments: 1) transfection with an expression vector carrying a drug resistance gene, 2) co-transfection with an expression vector and a vector that transiently expresses a cell surface marker, and 3) co-transfection with an expression vector and a vector carrying a different drug resistance gene. The cell selection procedures discussed herein can be used to implement these specific strategies. The invention can also be used to re-transfect cell with expression vectors encoding specific recombinant proteins of interest such as when an expression vector encodes two polypeptide sequences (immunoglobin heavy and light chains). Preferred expression involves coordinate expression of both polypeptide chains. These specific methods and others discussed herein find a variety of uses including facilitating selection and screening of cells.

The present invention is further illustrated by the following Examples. These Examples are provided to aid in the understanding of the invention and are not to be construed as a limitation thereof.

EXAMPLE I

Retransfection of CHO Cells for High Level Production of Recombinant Anti-tissue Factor (TF) Antibody 1. Vector Characterization A vector referred to as pJAIgG4TF.A8 (FIG. 1A) was constructed to express chimeric anti-tissue factor (TF) heavy and light immunoglobulin chains in mammalian cells. Initial transient transfection experiments were carried out to test antibody expression from the pJAIgG4TF.A8 vector. COS cells were transiently transfected using the Qiagen lipofectin reagent. Briefly, 2.5×10$^5$ cell/well were seeded in a 6 well plate and incubated for 24 hours at 37° C. Two micrograms of pJAIgG4TF.A8 DNA were mixed with 100 µl of IMDM. To make the lipid complex, 10 µl of lipids was added to the DNA solution. The mixture was vortexed and incubated at room temperature for 5 minutes. While DNA was forming the lipid complex, the cells were washed with PBS. The DNA-lipid mixture was mixed with 600 μl of 10% SSM [10% fetal bovine serum (FBS) supplemented CellGro IMDM (MediaTech) media] and added to the washed cells. The cells were incubated with lipid complexes for 3 hours at 37° C. and 10% $CO_2$. The transfected cells were washed with PBS, fed 2 ml of 10% SSM and incubated for 72 hours at 37° C. and 10% $CO_2$. The culture supernatant was tested for antibody production.

2. ELISA to Test Antibody Production

To detect the presence of the human IgG4 antibody, a human HC/kappa-specific sandwich ELISA was developed. Briefly, Maxisorp 96 well plates (NUNC) were coated with 100 μl of 1 μg/ml Goat anti-Human IgG-Fc (Fab) in R5 buffer (10 mM Tris-HCl, pH 8.5) and incubated at 4° C. overnight. The wells were then washed with R55 buffer (2 mM Imidazole, 7.5 mM NaCl, 0.02% Tween-20) once, covered with a plastic film and stored at 4° C. until used. To assay antibody production, the R55 was removed and 100 μl of transfectant supernatant was added to the coated wells. After 30 minutes at 37° C., the wells were washed 6 times with R55 buffer and 100 μl of a 1:800 dilution (in PBS containing 10% FBS) of an anti-human Kappa chain-HRP antibody (Southern Biotech) was added. The plates were then incubated at 37° C. and washed 6 times with 400 μl of R55 buffer. To detect the presence of the probe antibody, 100 μl of 1× ABTS substrate (Kirkegaard & Perry Labs) was added for 4 minutes and followed by 100 μl of ABTS quench buffer (Kirkegaard & Perry Labs). Absorbance was read at 405 nm. Purified human IgG4 protein served as a positive control. The results from such an assay showed that the anti-TF IgG4 antibody was produced by COS cell transiently tranfected by the pJAIgG4TF.A8 vector.

3. ELISA to Test Antibody Specificity

A second sandwich ELISA was developed to specifically detect antibody binding to human tissue factor. Maxisorp 96 well plates (NUNC) were coated overnight at 4° C. with 100 μl of 500 ng/ml recombinant human -TF in R65 buffer (100 mM Sodium Bicarbonate, pH 8.2). The next day the plates were washed with R55 buffer, covered and stored at 4° C. until used. To detect anti-TF antibody production, the R55 was removed and 100 μl of transfectant supernatant was added to the coated wells. After 30 minutes at 37° C., the wells were wash 6 times with R55 buffer and 100 μl of a 1:800 dilution (in PBS containing 10% FBS) of an anti-human Kappa chain-HRP (Southern Biotech) was added. The plates were then incubated at 37° C. and washed 6 times with 400 pi of R55 buffer. To detect the presence of the probe antibody, 100 μl of 1× ABTS substrate was added for 4 minutes and followed by 100 μl of ABTS quench buffer. Absorbance was read at 405 nm. Purified mouse H36.D2 anti-TF protein served as a positive control. The results from such an assay showed that the anti-TF IgG4 antibody was produced by COS cell transiently tranfected by the pJAIgG4TF.A8.

4. Initial Stable Transfection of CHO Cells

To generate a stable cell line expressing the recombinant anti-TF antibody, CHO.K1 cells were transfected with the pJAIgG4TF.A8 vector. Briefly, 100 μg of pJAIgG4TF.A8 DNA was linearized by digesting with Pvul at 37° C. for about 4 hours. CHO.K1 cells (ATCC CCL-61) were diluted to a concentration of $1.25\times10^7$ cell/ml. A volume of 800 μl of cells was added to an 0.4 cm electroporation cuvette and incubated on ice for 10 minutes. Twenty five micrograms of pJAIgG4TF.A8 DNA were added, mixed with the cells, and incubate for 10 minutes. The cells were then electroporated at 960 μF and 250 V. Following a 10 minute incubation on ice, the cell suspension was added to a T25 flask with 10 ml 10% SSM and incubated overnight at 37° C. in 10% $CO_2$. Twenty-four hours later, the cells were harvested by incubation with trypsin-PBS, resuspended in PBS and diluted in G418 supplemented media at 1:9, 1:27 and 1:81. The transfected cells were plated at 100 μl/well in 96 well plates and Incubated at 37° C. in 10% $CO_2$.

Culture supernatant from the transfected cells was tested for antibody production as described above. Positive clones were selected and expanded. Clone H9 from row H column 9 of the 1:27 dilution plate was selected as a high antibody level producer.

This cell line was cloned by limiting dilution. Briefly, the selected clone was diluted to 1000 cell/ml in PBS. A series of 1:10 dilutions in 10% SSM were made to obtained 1 cell/ml. From these dilutions, 100 μl/well were plated in 96 well flat bottom plates. These plates were incubated at 37° C. in 10% $CO_2$. After three days of incubation, 100 μl/well of 10% SSM was added to each well. Three weeks later, single colonies started to become apparent. Only single colonies were tested for antibody production by ELISA. Clones with high levels of antibody production were amplified and selected. Clone H9g12 was selected as highest producer and analyzed for antibody production in static culture.

The selected clones were harvested by treatment with trypsin, resuspended at a concentration of $1\times10^5$ cell/ml in 10 ml of 10% SSM media and added to a T-25 tissue culture flask. The cells were incubate at 37° C. in 10% CO2 for 21 days or until 80% cell death. The cell suspension was centrifuged and the supernatant was tested for Ab production by ELISA assay. The maximum antibody production of the H9g12 clone was 3.5 μg/ml.

5. Stable Re-transfection of the CHO-H9g12 Cell Line

This method was developed to add more copies of the genes of interest to the genome of a stable Ab-producing cell line. To proceed with this method, clone H9g12 was co-transfected with a mixture of the anti-human TF mega vector pJAIgG4TF.A8 and pMACS. The pMACS vector allows for the transient expression of a membrane bound CD4 protein. To co-transfect the H9g12 cell line, 800 μl of a $1.25\times10^7$ cell/ml suspension was added to a 0.4 cm electroporation cuvette and incubated on ice for 10 minutes. A 3:1 molar ratio of pJAIgG4TF.A8 and pMACS DNA (40 μl of 1 μg/ml Pvul-linearized pJAIgG4TF.A8 and 5 μl of 1 μg/ml supercoiled pMACS) was added to the cells. After incubating on ice for 10 minutes, the cells were electroporated at 960 μF and 250 V. The cells were incubate at 37° C. for 10 minutes, diluted to 10 ml 10% SSM in a T25 flask and incubated 72 hours at 37° C. in 10% $CO_2$ to allow the transient expression of the CD4 protein. At this time, the cells were treated with 5 ml of PBE (EDTA in PBS solution) at room temp until they detached. Cells were wash once, resuspended in 380 μl of PBE and labeled with 80 μl of an antibody specific to the cell surface-expressed human CD4 molecule. This antibody was covalently bound to a magnetic bead. Following incubation for 15 to 20 minutes at 4° C., the antibody labeled-cells were applied to a magnetic column. Transfected cells that express the CD4 on their surfaces are expected to bind the magnetic column. The untransfected cells were washed through the column with 1 ml PBE. The bound cells were then eluted from column by removing column from magnetic field and passing 1 ml of PBE through the column. CD4-expressing cells were diluted in 199 ml of 10% SSM supplemented with G418 (1.5 mg/ml) and plated in 96 well flat bottom plate. The plates were incubated at 37° C. in 10% $CO_2$.

To test for antibody production, Maxisorp 96 well plates (NUNC) were coated with 100 μl of 1 μg/ml Goat anti-Human IgG-Fc (Fab) (Pierce) as described above. The media from re-transfected cells was changed 24 hours prior to testing. Five microliters of the transfectant 24 hour supernatant were added to 95 μ of 10% FBS-PBS. The diluted supernatant was added to the coated wells and was incubated for 60 minutes at 37° C. The wells were washed 6 times with R55 buffer and an anti-human kappa chain antibody-HRP (Southern Biotech) was used to detected recombinant antibody present in the supernatant as described above. Purified human IgG4 protein (Biodesign) served as a positive control and was used to establish a standard curve for antibody concentration.

The clone selection was accomplished by comparing antibody production rates to cell number. Briefly, the high producing clones were trypsin treated and counted. Using the calculated antibody production rate and the number of cells, values for the μg antibody/$10^6$ cells/24 hour were determined. High producer clones were amplified to 24 well/plates and expanded. The clone selected was named 3D2.

For limited dilution cloning, the selected clones were serially diluted in 10% SSM, seeded in 96 well flat bottom plates, incubated as described above. After three weeks, single colonies were tested for antibody production by ELISA. Clones with high levels of antibody production were amplified and selected. Clone 3D2A9 showed 2.58 μg antibody/$10^6$ cells/24 hour and was selected as the best clone. Analysis of antibody production in static culture was initiated for this clone.

Static cultures of the 3D2A9 clone were initiated by adding a concentration of 2×$10^5$ cells/ml in 10 ml of 10% SSM media to a T-25 tissue culture flask. The flasks were incubated at 37° C. in 10% CO2 for 21 day or until 80% cell death. The cell suspension was centrifuged and supernatant was tested for antibody production by ELISA. The maximum antibody production of the 3D2A9 clone was 21 μg/ml. This production level was 7 fold higher than the first transfection clone.

6. Third Stable Transfection

To further increase the antibody production level of the transfected cells, the clone 3D2A9 was again co-transfected with a mix of the anti-human TF mega vector pJAlgG4TF.A8 and pMACS. To cotransfect this cell line, 800 μl of a 1.25×$10^7$ cell/ml suspension was added to a 0.4 cm electroporation cuvette and incubated on ice for 10 minutes. A 3:1 molar ratio of pJAlgG4TF.A8 and pMACS DNA (50 μl of 1 μg/ml PvuI-linearized pJAIgG4TF.A8 and 5 μl of 1 μg/ml supercoiled pMACS) was added to the cells. After incubating on ice for 10 minutes, the cells were electroporated at 960 μF and 250 V. The cells were incubate at 37° C. for 10 minutes, added to 10 ml 10% SSM in a T25 flask and incubated 48 hours at 37° C. in 10% $CO_2$ to allow the transient expression of the CD4 protein. At this time, the transfected cells were labeled with the anti-CD4 magnetic beads and selected on the magnetic column as described above. CD4-expressing cells were diluted in 200 ml of 10% SSM supplemented with G418 (1.5 mg/ml). The cell suspension was plated in 96 well flat bottom plate. The plates were incubated at 37° C. in 10% $CO_2$ for approximately three weeks.

Maxisorp 96 well plates (NUNC) were coated with 100 μl of 1 μg/ml Goat anti-Human IgG-Fc (Fab) (Pierce) in R5 as described above. To assay antibody production rates, media from re-transfected cells was changed 24 hours prior to testing. Five microliters of the transfectant 24 hour supernatant were added to 95 μl of 10% FBS-PBS. The diluted supernatant was added to the coated wells and was incubated for 60 minutes at 37° C. The wells were washed 6 times with R55 buffer and an anti-human Kappa chain antibody-HRP (Southern Biotech) was used to detected recombinant antibody present in the supernatant as described above. A purified anti-TF chimeric antibody served as a positive control and was used to establish a standard curve for antibody concentration. Results from this test allowed the selection of high antibody producing clones that were then amplified to a 12 well plate. These clones were grown to 80% of the well and 24 hour supernatants was tested. A 1:100 dilution of the 24 hr culture supernatant was tested by ELISA. Cells were also counted and μg/$10^6$ cells/24 hour antibody production values were determine. Highest antibody producing mother clones A9B11 and A9F12 was selected based on these values.

Selected clones were serially diluted in 10% SSM, seeded in 96 well flat bottom plates, incubated as described above. After three weeks, single colonies were tested for antibody production by ELISA. Clones with a high antibody production level were amplified. The primary clones A9F12C2 and A9AI 1B5 were found to have the highest clones with an antibody production rate of 30 to 40 μg/$10^6$ cells /24 hours. The clones were expanded for static cultures.

Static cultures of the A9F12C2 clone were initiated by adding a concentration of 2×$10^5$ cells/ml in 10 ml of 10% SSM media to a T-25 tissue culture flask. The flasks were incubated at 37° C. in 10% $CO_2$ for 21 day or until 80% cell death. The cell suspension was centrifuged and supernatant was tested for Ab production by ELISA The maximum antibody production of the A9F12C2 clone was 52 μg/ml. This production level was 2 fold higher than the second transfection clone.

The selected clone A9F12C12 was serially diluted in 10% SSM, seeded in 96 well flat bottom plates, incubated as described above. After three weeks, single colonies were tested for antibody production by ELISA. The secondary clone A9F12C2E7 was found to have the highest antibody production rate and was expanded for static cultures. These static cultures were carried out as described above.

To determine the antibody concentration in the static culture supernatants, 5 μl of A9F12C2E7 cell supernatant was added to 4,995 μl of 10% PBS. This diluted supernatant was assayed for the chimeric antibody by the antibody ELISA described above. As a positive control, the purified anti-TF chimeric antibody was used. The results from this test indicated that the A9F12C2E7 secondary clone had a maximum antibody production level of 52.6 μg/ml in static culture.

The selected clone A9F12C12E7 was serially diluted in 10% SSM, seeded in 96 well flat bottom plates, incubated as described above. After three weeks, single colonies were tested for antibody production by ELISA. The tertiary clone A9F12C2E7B4 was selected as the highest producer and was expanded for static culture. These cultures were initiated as previously described.

Figure 2:
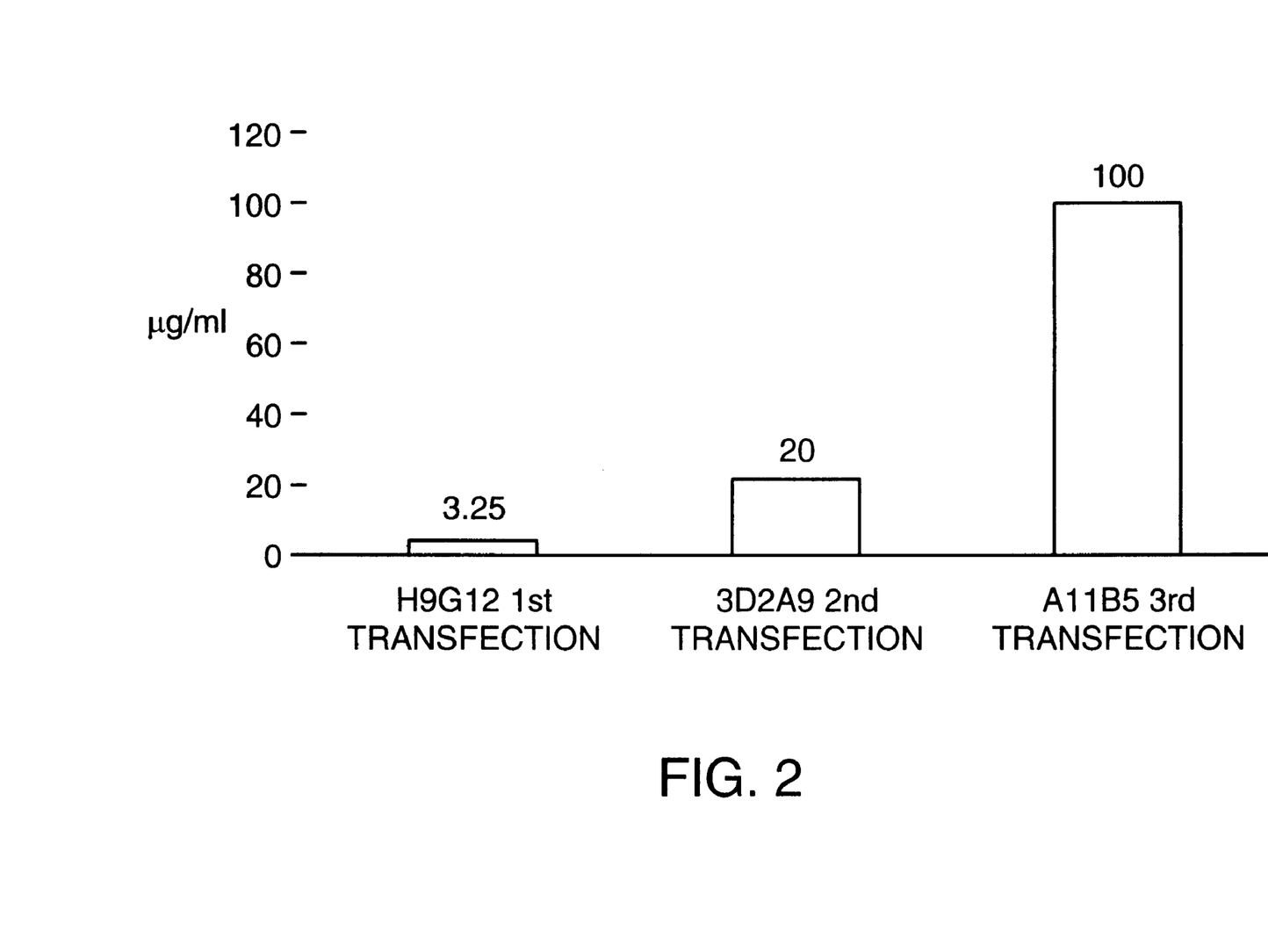
FIG. 2 is a graph showing high level production of recombinant chimeric anti-TF antibody in T25 flask static cultures. Recombinant cell lines producing high levels of the anti-TF antibody were isolated following three sequential transfections. High producing recombinant cell lines were designated H9G12, 3D2A9, and A11B5, respectively.

To determine the antibody concentration in the static culture supernatants, 5 μl of A9F12C2E7 cell supernatant was added to 4,995 μl of 10% PBS. This diluted supernatant was assayed for the chimeric antibody by the antibody ELISA described above. As a positive control, the in-house purified anti-TF chimeric antibody was used. The maximum antibody production for clone A9F12C2E7B4 was 102.3 μl/ml (FIG. 2). The cell line was amplified and frozen. Fifty vials at a concentration of 1×$10^6$ cells/ml were made as an initial seed cell bank and were stored in liquid nitrogen. Name designation for cell line is cH36 (chimeric H36).

7. Bioreactor Injection

Figure 3:
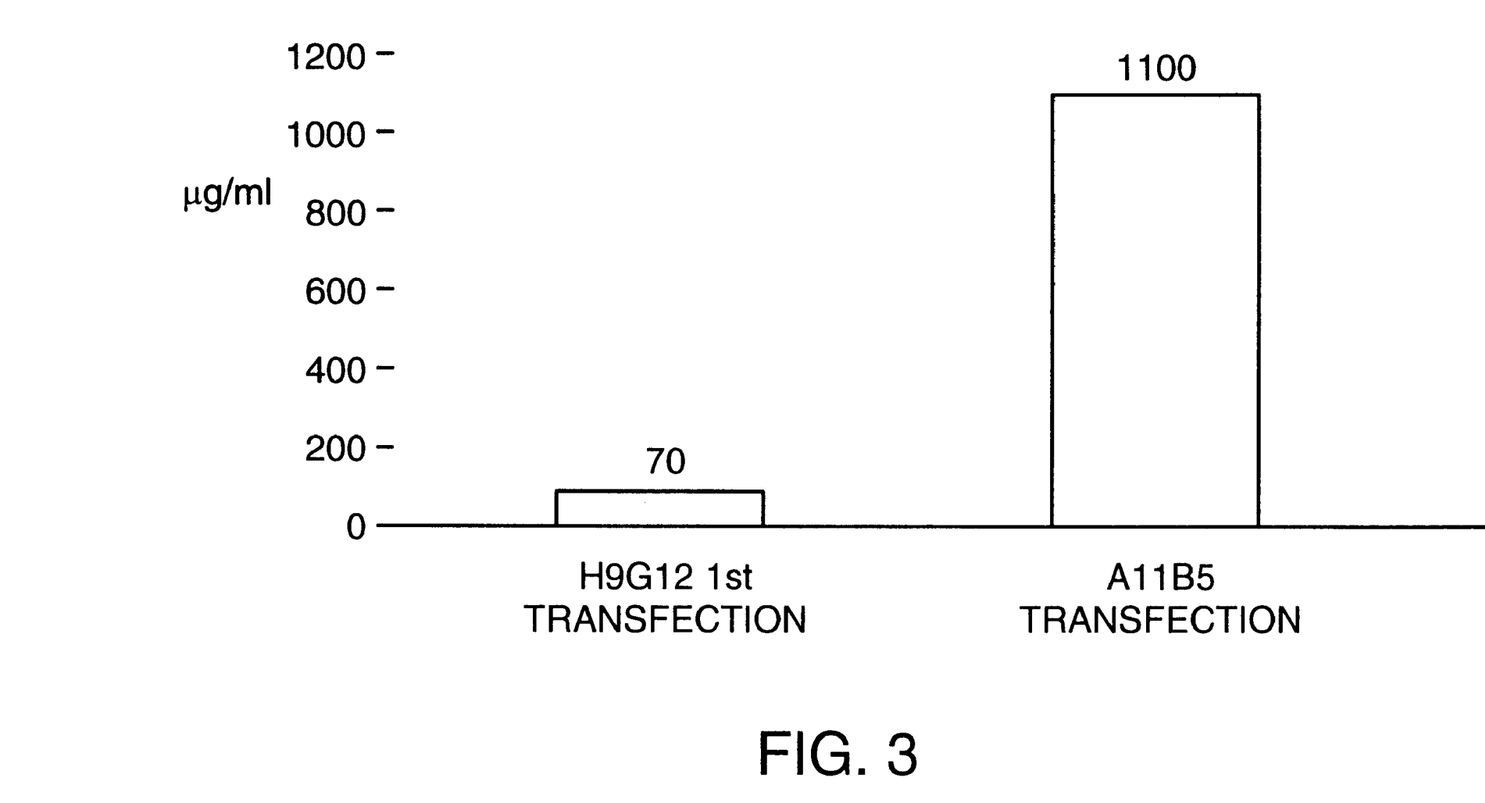
FIG. 3 is a graph showing high level production of recombinant chimeric anti-TF in a bioreactor. Recombinant cell lines producing high levels of the anti-TF antibody were isolated following three sequential transfections. High producing recombinant cell lines were designated H9G12 and A11B5 for lines isolated after the first and third transfections.

A hollow fiber bioreactor was set up as indicated in the manufacturer instructions. Selected clone was resuspended at $1 \times 10^8$ cells/ml in the correct volume of 30% SSM and injected into the bioreactor. The bioreactor was then run as specified by manufacturer instructions. Maximum production was tested by ELISA as described above. The first transfection primary clone H9g12 produced 70 μg antibody/ml at a maximum as compared to the third transfection primary clone A11B5 which produced 1,100 μg antibody/ml (FIG. 3).

EXAMPLE 2
Generation of Cell Lines for Production of Recombinant HLA-DR2 MHC Class II Molecule

1. Vector Characterization

A vector referred to as pDRHK (FIG. 1B) was constructed for mammalian expression of soluble single-chain HLA-DR2/MBP molecule fused to the human immunoglobulin kappa constant domain. Initial transient transfection experiments were carried out to test protein expression from the pDRHK vector. COS cells were transiently transfected using the Qiagen lipofectin reagent. Briefly, $2.5 \times 10^5$ cell/well were seeded in a 6 well plate and incubated for 24 hours at 37° C. Two micrograms of pDRHK DNA were mixed with 100 μl of IMDM. To make the lipid complex, 10 μl of lipids was added to the DNA solution. The mixture was vortexed and incubated at loom temperature for 5 minutes. While DNA was forming the lipid complex, the cells were washed with PBS. The DNA-lipid mixture was mixed with 600 μl of 10% SSM and added to the washed cells. The cells were incubated with lipid complexes for 3 hours at 37° C. and 10% $CO_2$. The transfected cells were washed with PBS, fed 2 ml of 10% SSM and incubated for 72 hours at 37° C. and 10% $CO_2$. The supernatant was tested for recombinant DR2/MBP-CK production.

2. ELISA to Detect sc- DR2/MBP-Cκ Production

To detect the presence of the sc-DRZ/MBP-C6, a human 6/HLA-DR-specific sandwich ELISA was developed. Briefly, Maxisorp 96 well plates (NUNC) were coated with 100 μl of 1 μg/ml Goat anti-human IgG-kappa in PBS and incubated at 4° C. overnight. The wells were then washed with R55 buffer once, covered with a plastic film and stored at 4° C. until used. To assay recombinant protein production, the R55 was removed and 100 μl of transfectant supernatant was added to the coated wells. After 60 minutes at 37° C., the wells were wash 6 times with R55 buffer and 100 μl of a 1:1000 dilution (in PBS containing 10% FBS) of an anti HLA-DR antibody L243 conjugated to HRP (Anergen, ATCC HB-55) was added. The plates were then incubated at 37° C. and washed 6 times with 400 μg of R55 buffer. To detect the presence of the probe antibody, 100 μl of 1x ABTS substrate was added for 5 minutes and followed by 100 μl of ABTS quench buffer. Absorbance was read at 405 nm. The results from such an assay showed that the scDR2/MBP-Cκ fusion protein was produced by COS, cell transiently tranfected by the pDRHK vector.

3. Initial Stable Transfection

To generate a stable cell line expressing the sc-DR2/MBP-Cκ fusion protein, CHO.K1 cells were transfected with the pDRHK vector. Briefly, 100 μg of pDRHK DNA was linearized by digesting with Pvul at 37° C. for about 4 hours. CHO.K1 cells (ATCC CCL-61) were diluted to a concentration of $1.25 \times 10^7$ cell/ml. A volume of 800 μl of cells was added to an 0.4 cm electroporation cuvette and incubated on ice for 10 minutes. Twenty micrograms of pDRHK DNA were added, mixed with the cells, and incubate for 10 minutes. The cells were then electroporated at 960 μF and 250 V. Following a 10 minute incubation on ice, the cell suspension was added to a T25 flask with 10 ml 10% SSM and incubated overnight at 37° C. in 10% $CO_2$. Twenty-four hours later, the cells were harvested by incubation with trypsin-PBS, resuspended in PBS and diluted in G418 supplemented media at 1:9, 1:27 and 1:81. The transfected cells were plated at 100 μl/well in 96 well plates and incubated at 37° C. in 10% $CO_2$.

Supernatant from cells from different 96 well plates were tested as described above. Positives clones were selected and expanded. Clone A5 from row A column 5 of the 1:27 plate was selected as a high producer. This cell line was subcloned by limiting dilution as described above. After screening, clone A5B4 was selected as highest producing cell line and static culture was initiated.

The selected clones were harvested by treatment with trypsin, resuspended at a concentration of $1 \times 10^5$ cells/ml in 10 ml of 10% SSM media and added to a T-25 tissue culture flask. The cells were incubate at 37° C. in 10% $CO_2$ for 21 days or until 80% cell death. The cell suspension was centrifuged and the supernatant was tested for recombinant DR2 production by ELISA assay. Recombinant sc-DR2/MBP-C6 fusion production by the A5B4 clone was 20 μg/ml.

4. Stable Re-transfection

To proceed with this method, clone A5B4 is co-transfected with a mix of pDRHK and pMACS. A volume of 800 μl of a $1.25 \times 10^7$ cell/ml suspension was added to a 0.4 cm electroporation cuvette an incubated on ice for 10 minutes. A 3:1 molar ratio of pDRHK and pMACS DNA (30 μl of 1 μg/ml Pvul linearized pDRHK and 5 μl of 1 μg/ml supercoiled pMACS) was added to the cells. After incubating on ice for 10 minutes, the cells were electroporated at 960 μF and 250 V. The cells were incubate at 37° C. for 10 minutes, diluted to 10 ml 10% SSM in a T25 flask and incubated 72 hours at 37° C. in 10% $CO_2$ to allow the transient expression of the CD4 protein. At this time, the cells were treated with 5 ml of PBE at room temperature until they detached. Cells were wash once, resuspended in 380 μl of PBE and labeled with 80 μl of an antibody specific to the cell surface-expressed human CD4 molecule. This antibody was covalently bound to a magnetic bead. Following incubation for 15 to 20 minutes at 4° C., the antibody labeled-cells were applied to a magnetic column. Transfected cells that express the CD4 on their surfaces are expected to bind the magnetic column. The untransfected cells were washed through the column with 1 ml PBE. The bound cells were then eluted from column by removing column from magnetic field and passing 1 ml of PBE through the column. CD4-expressing cells were diluted in 199 ml of 10% SSM supplemented with G418 (1.5 mg/ml) and plated in 96 well flat bottom plate. The plates were incubated at 37° C. in 10% $CO_2$.

After 3 weeks, the supernatant from different 96 well plates were tested for recombinant protein as described above. Positive clones were selected and expanded. Clone $DR2^2$ was selected as the highest producer. This cell line was frozen.

A vial of $DR2^2$ clone was quick thawed in a 37° C. water bath and grown to 95% viability. The cells were serially diluted for limited dilution cloning as described above. After three weeks of growth, single colonies were tested for sc-DR2-Cκ production by ELISA. The clones with the highest production levels were amplified and selected. Clone $DR2^2$-H4 was identified as the best producer. Static cultures were carried out as described above and recombinant protein production from the $DR2^2$-H4 clone was found to be 100 ng/ml.

4. Third Stable Transfection

Figure 4:
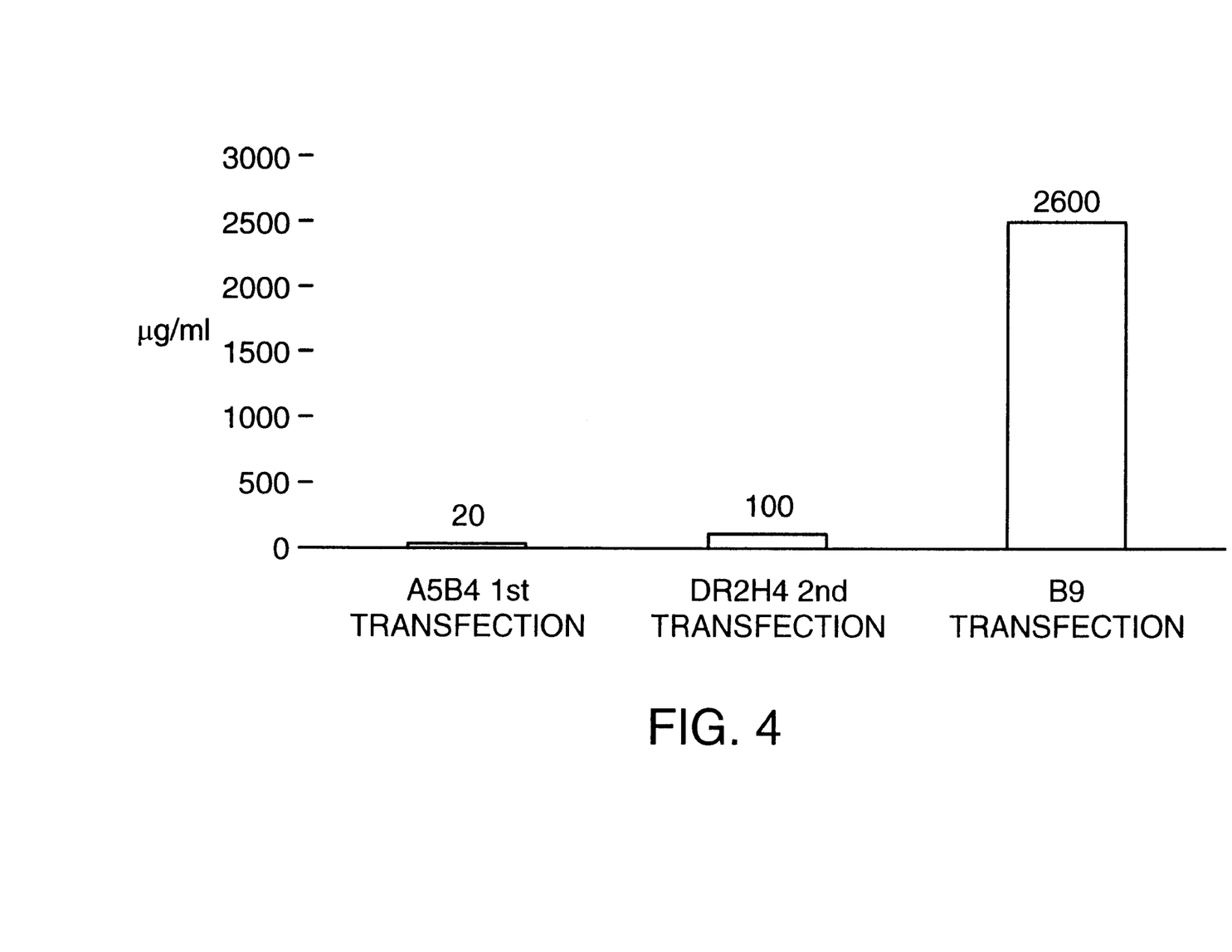
FIG. 4 is a graph showing high level production of recombinant sc-DR2/MBP-Cκ production in T25 flask static cultures. Recombinant cell lines producing high levels of the sc-DR2/MBP-Cκ fusion protein were isolated following three sequential transfections. High producing recombinant cell lines were designated A5B4, DR2H4, and B9 respectively.

To further increase recombinant protein production, primary clone DR2²-H4 was co-transfected with a mixture of pDRHK and pPUR (Clonetech), a vector carrying a gene that confers resistance to puromycin. Briefly, 800 µl of a $1.25 \times 10^7$ cell/ml suspension was added to a 0.4 cm electroporation cuvette and incubated on ice for 10 minutes. A 3:1 molar ratio of pDRHK and pMACS DNA (25 µl of I µg/ml Pvullinearized pDRHK and 5 µl of 1 µg/ml Pvul-linearized pPUR) was added to the cells. After incubating on ice for 10 minutes, the cells were electroporated at 960 µF and 250 V. the cells were incubate at 37° C. for minutes, added to 10 ml 10% SSM in a T25 flask and incubated 48 hours at 37° C. in 10% $CO_2$. The cells were then harvested by trypsin treatment, centrifuged and resuspended in 10% SSM containing G418 (1.5 mg/ml) and Puromycin (20 µg/ml). The cells were plated in 96 well flat bottom plates and incubated at 37° C. in 10% $CO_2$. After colonies were apparent, the culture media was tested for recombinant protein. Clones A9 and B9 were found to be the highest producers and were tested in static cultures as described above. The static culture recombinant protein production was 1,800 ng/ml for A9 and 2,108 for B9 (FIG. 4).

These cell lines were subcloned by limited dilution cloning and tested for recombinant protein production. Primary clones A9D5, A9G4, A9C7, B9H3, B9G4, and B9H5 were identified as having scDR2/MBP-Cκ production rates of 200 to 300 ng/ml in 24 hours. Recombinant protein production by these clones in static cultures was carried out as described above.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method for producing a cell line featuring increased expression of an amino acid sequence, the method comprising:
    a) introducing into host cells a first vector comprising a first selectable sequence operably linked to a segment encoding the amino acid sequence,
    b) culturing the host cells under conditions conductive to selecting the first vector,
    c) isolating cells expressing the amino acid sequence at a first expression level (first high expressing cells),
    d) introducing into the cells expressing at the first expression level a second vector encoding the amino acid sequence,
    e) subjecting the cells to conditions conductive to expressing the amino acid sequence at a second expression level higher than the first expression level; and
    f) isolating the cells expressing the amino acid sequence at the second expression level to produce the cell line (second high expressing cells),
wherein the isolation further comprises selecting cells expressing a cell-surface marker.

2. The method of claim 1, wherein the method further comprises:
    g) introducing into the cells expressing at the second expression level a third vector encoding the amino acid sequence and subjecting the cells to conditions conductive to expressing the amino acid sequence at a third expression level higher than the second expression level; and
    h) isolating the cells expressing the amino acid sequence at the third expression level to produce the cell line (third high expressing cells).

3. The method of claim 2, wherein the method further comprises introducing into the third high expressing cells a vector encoding the amino acid sequence and subjecting the cells to conditions conducive to expressing the amino acid sequence at a level higher than the third expression level and repeating the introduction and subjecting steps at least once to isolate a cell line expressing the amino acid sequence at a higher level than the third high expressing cells.

4. The method of claim 1, wherein step b) of the method further comprises growing the cells in selective media comprising at least one drug selective for the first selectable sequence.

5. The method of claim 1, wherein step d) of the method further comprises introducing into the cells a fourth vector and subjecting the cells to conditions conducive to expressing the amino acid sequence at the second expression level.

6. The method of claim 5, wherein the fourth vector further comprises a second selectable sequence.

7. The method of claim 6, wherein the fourth vector further comprises a second selectable sequence operably linked to a segment encoding the amino acid sequence.

8. The method of claim 6, wherein the method further comprises growing the cells in selective media containing at least one drug selective for the second selectable sequence.

9. The method of claim 1, wherein the selectable cell-surface marker is a cell surface receptor, glycoprotein, carbohydrate, protein, lipoprotein, major histocompatibility (MHC/HLA) complex, antibody, antigen; or functional fragment thereof.

10. The method of claim 9, wherein the selectable cell-surface glycoprotein marker is a CD (cluster of differentiation) glycoprotein.

11. The method of claim 4, wherein the drug is aminoglycoside antibiotic (G418), hygromycin B (hmb), puromycin, or neomycin.

12. The method of claim 2, wherein step g) of the method further comprises introducing into the cells a fifth vector and subjecting the cells to conditions conductive to expressing the amino acid sequence at the third expression level.

13. The method of claim 12, wherein the fifth vector further comprises a third selectable sequence.

14. The method of claim 13, wherein the third selectable sequence is operably linked to a segment encoding the amino acid sequence.

15. The method of claim 13, wherein the method further comprises growing the cells in selective media comprising at least one drug selective for a third selectable sequence.

16. The method of claim 1, wherein at least one of the first and the second vectors is introduced into the cells between from about 2 to about 20 times.

17. The method of claim 2, wherein the third vector is introduced into the cells from between about 2 to about 20 times.

18. The method of claim 1, wherein the cell surface marker is encoded by at least one of the first and the second vectors.

19. The method of claim 1, wherein the second high expressing cells express from between about 3 to about 40 fold more of the ammo acid sequence relative to the first high expressing cells as determined by antibody reactivity.

20. The method of claim 2, wherein the third high expressing cells express from between about 3 to about 40 fold more of the amino acid sequence relative to the second high expressing cells as determined by antibody reactivity.

21. The method of claim 1, wherein the amino acid sequence encodes an immunoglobulin heavy to light chain or a functional fragment thereof.

22. The method of claim 2, wherein each of the vectors independently encodes a first drug resistance gene, a cell surface marker or a second drug resistance gene, and further wherein each of the vectors is operably linked to the amino acid sequence.

23. A cell line produced by the method of claims 1, 2 or 3.

24. A method for producing a cell line featuring increased expression of an amino acid sequence, the method comprising:
  a) introducing into host cells a first vector comprising a first selectable sequence operably linked to a segment encoding the amino acid sequence,
  b) culturing the host cells under conditions conducive to selecting the first vector,
  c) isolating cells expressing the amino acid sequence at a first expression level (first high expressing cells),
  d) introducing into the cells expressing at the first expression level a second vector encoding the amino acid sequence, the method further comprising introducing into the cells a third vector comprising a sequence encoding a selectable cell surface marker,
  e) subjecting the cells to conditions conducive to expressing the amino acid sequence at a second expression level higher than the first expression level; and
  f) isolating the cells expressing the amino acid sequence at the second expression level to produce the cell line (second high expressing cells).

25. A method for producing a cell line featuring increased expression of an amino acid sequence, the method comprising:
  a) introducing into host cells a first vector comprising a first selectable sequence operably linked to a segment encoding the amino acid sequence,
  b) culturing the host cells under conditions conducive to selecting the first vector,
  c) isolating cells expressing the amino acid sequence at a first expression level (first high expressing cells),
  d) introducing into the cells expressing at the first expression level a second vector encoding the amino acid sequence, the method further comprising introducing into the cells a third vector comprising a sequence encoding a selectable cell surface marker operably linked to a segment encoding the amino acid sequence,
  e) subjecting the cells to conditions conducive to expressing the amino acid sequence at a second expression level higher than the first expression level; and
  f) isolating the cells expressing the amino acid sequence at the second expression level to produce the cell line (second high expressing cells).

26. A method for producing a cell line featuring increased expression of an amino acid sequence, the method comprising:
  a) introducing into host cells a first vector comprising a first selectable sequence operably linked to a segment encoding the amino acid sequence,
  b) culturing the host cells under conditions conducive to selecting the first vector,
  c) isolating cells expressing the amino acid sequence at a first expression level (first high expressing cells),
  d) introducing into the cells expressing at the first expression level a second vector encoding the amino acid sequence, the method further comprising introducing into the cells a third vector comprising a sequence encoding a selectable cell surface marker operably linked to a segment encoding the amino acid sequence,
  e) subjecting the cells to conditions conducive to expressing the amino acid sequence at a second expression level higher than the first expression level; and
  f) isolating the cells expressing the amino acid sequence at the second expression level to produce the cell line (second high expressing cells),
wherein the method further comprises isolating the cells expressing the cell surface marker by at least one of chromatography, cell panning, flow cytometry, immunoprecipitation, or antibody binding.

27. The method of claim 24, 25 or 26, wherein step b) of the method further comprises growing the cells in selective media comprising at least one drug selective for first selectable sequence.

28. A method for producing a cell line featuring increased expression of an amino acid sequence, the method comprising:
  a) introducing into host cells a first vector comprising a first selectable sequence operably linked to a segment encoding the amino acid sequence,
  b) culturing the host cells under conditions conducive to selecting the first vector,
  c) isolating cells expressing the amino acid sequence at a first expression level (first high expressing cells),
  d) introducing into the cells expressing at the first expression level a second vector encoding the amino acid sequence,
  e) subjecting the cells to conditions conducive to expressing the amino acid sequence at a second expression level higher than the first expression level; and
  f) isolating the cells expressing the amino acid sequence at the second expression level to produce the cell line (second high expressing cells),
  g) introducing into the cells expressing at the second expression level a third vector encoding the amino acid sequence and subjecting the cells to conditions conducive to expressing the amino acid sequence at a third expression level higher than the second expression level, the method further comprising introducing into the cells a fourth vector comprising a sequence encoding a selectable cell surface marker and subjecting the cells to conditions conducive to expressing the amino acid sequence at the third expression level; and
  h) isolating the cells expressing the amino acid sequence at the third expression level to produce the cell line (third high expressing cells).

29. A method for producing a cell line featuring increased expression of an amino acid sequence, the method comprising:
  a) introducing into host cells a first vector comprising a first selectable sequence operably linked to a segment encoding the amino acid sequence,
  b) culturing the host cells under conditions conducive to selecting the first vector,
  c) isolating cells expressing the amino acid sequence at a first expression level (first high expressing cells),
  d) introducing into the cells expressing at the first expression level a second vector encoding the amino acid sequence,
  e) subjecting the cells to conditions conducive to expressing the amino acid sequence at a second expression level higher than the first expression level; and f) isolating the cells expressing the amino acid sequence at the second expression level to produce the cell line (second high expressing cells), g) introducing into the cells expressing at the second expression level a third vector encoding the amino acid sequence and subjecting the cells to conditions conducive to expressing the amino acid sequence at a third expression level higher than the second expression level, the method further comprising introducing into the cells a fourth vector comprising a sequence encoding a selectable cell surface marker operably linked to a segment encoding the amino acid sequence and subjecting the cells to conditions conducive to expressing the amino acid sequence at the third expression level; and h) isolating the cells expressing the amino acid sequence at the third expression level to produce the cell line (third high expressing cells).

30. A method for producing a cell line featuring increased expression of an amino acid sequence, the method comprising:

a) introducing into host cells a first vector comprising a first selectable sequence operably linked to a segment encoding the amino acid sequence, b) culturing the host cells under conditions conducive to selecting the first vector, c) isolating cells expressing the amino acid sequence at a first expression level (first high expressing cells), d) introducing into the cells expressing at the first expression level a second vector encoding the amino acid sequence, e) subjecting the cells to conditions conducive to expressing the amino acid sequence at a second expression level higher than the first expression level; and f) isolating the cells expressing the amino acid sequence at the second expression level to produce the cell line (second high expressing cells), g) introducing into the cells expressing at the second expression level a third vector encoding the amino acid sequence and subjecting the cells to conditions conducive to expressing the amino acid sequence at a third expression level higher than the second expression level, the method further comprising introducing into the cells a fourth vector comprising a sequence encoding a selectable cell surface marker operably linked to a segment encoding the amino acid sequence and subjecting the cells to conditions conducive to expressing the amino acid sequence at the third expression level; and h) isolating the cells expressing the amino acid sequence at the third expression level to produce the cell line (third high expressing cells), wherein the method further comprises isolating the cells expressing the cell surface marker by at least one of chromatography, cell panning, flow cytometry, antibody binding, immunoprecipitation, and antibody binding.

31. A cell line produced by the method of claim 24, 25, 26, 27, 28, or 29.

32. The method of claim 2, wherein the third vector further comprises a sequence encoding the selectable cell surface marker.

33. The method of claim 1, 24, 25, 26, 27, 28, or 29, wherein the amino acid sequence encodes an immunoglobin heavy chain, an immunoglobin light chain; or a functional fragment thereof.

34. The method of claim 28, 30 or 33, wherein step b) of the method further comprises growing the cells in selective media comprising at least one drug selective for the first selectable sequence.

* * * * *